(12) United States Patent
Malandain

(10) Patent No.: US 7,618,418 B2
(45) Date of Patent: Nov. 17, 2009

(54) PLATE SYSTEM FOR MINIMALLY INVASIVE SUPPORT OF THE SPINE

(75) Inventor: Hugues F. Malandain, Mountain View, CA (US)

(73) Assignee: Kyphon SARL (CH)

( * ) Notice: Subject to any disclaimer, the term of this patent is extended or adjusted under 35 U.S.C. 154(b) by 1080 days.

(21) Appl. No.: 11/019,918

(22) Filed: Dec. 20, 2004

(65) Prior Publication Data

US 2005/0234456 A1 Oct. 20, 2005

Related U.S. Application Data

(63) Continuation-in-part of application No. 10/826,684, filed on Apr. 16, 2004, now Pat. No. 7,524,323.

(51) Int. Cl.
*A61B 17/56* (2006.01)
(52) U.S. Cl. ...................................... 606/60
(58) Field of Classification Search ................ 606/54, 606/60, 246–253, 264–275, 280–296
See application file for complete search history.

(56) References Cited

U.S. PATENT DOCUMENTS

| | | | |
|---|---|---|---|
| 3,779,240 A | 12/1973 | Kondo |
| 4,493,317 A | 1/1985 | Klaue |
| 4,763,644 A | 8/1988 | Webb |
| 4,805,602 A | 2/1989 | Puno et al. |
| 4,946,458 A | 8/1990 | Harms et al. |
| 5,005,562 A | 4/1991 | Cotrel |
| 5,053,036 A | 10/1991 | Perren et al. |
| 5,057,111 A | 10/1991 | Park |
| 5,129,388 A | 7/1992 | Vignaud et al. |
| 5,129,899 A | 7/1992 | Small et al. |
| 5,147,361 A | 9/1992 | Ojima et al. |
| 5,151,103 A | 9/1992 | Tepic et al. |
| 5,171,279 A | 12/1992 | Mathews |
| 5,176,678 A | 1/1993 | Tsou |
| 5,176,679 A | 1/1993 | Lin |
| 5,180,381 A | 1/1993 | Aust et al. |
| 5,207,678 A | 5/1993 | Harms et al. |
| 5,234,431 A | 8/1993 | Keller |
| 5,246,442 A | 9/1993 | Ashman et al. |

(Continued)

FOREIGN PATENT DOCUMENTS

DE 94 02 695 U1 4/1994

(Continued)

*Primary Examiner*—Thomas C Barrett
*Assistant Examiner*—Michael J Araj

(57) ABSTRACT

An implantable medical device and methods of use thereof are provided for supporting a structure. The structure supported can include a bony structure. The device is comprised of a support having a top portion, a bottom portion having a bottom surface and one or more apertures passing therethrough. The bottom surface of the support includes a receiver configured to receive a plurality of anchor assemblies of one or multiple types. Each of the anchor assemblies includes a means for locking the anchor assembly to the support element, and a base having a head and a means for locking the base to the anchor assembly. When assembled, the head of the base for one anchor assembly type may not pass through the support. In contrast, the head of the base for a second anchor assembly type is passable through the support.

18 Claims, 7 Drawing Sheets

U.S. PATENT DOCUMENTS

| | | |
|---|---|---|
| 5,253,406 A | 10/1993 | Shere et al. |
| 5,261,909 A | 11/1993 | Sutterlin et al. |
| 5,269,784 A | 12/1993 | Mast |
| 5,290,288 A | 3/1994 | Vignaud et al. |
| 5,324,290 A | 6/1994 | Zdeblick et al. |
| 5,360,431 A | 11/1994 | Puno et al. |
| 5,395,371 A | 3/1995 | Miller et al. |
| 5,429,639 A | 7/1995 | Judet |
| 5,443,467 A | 8/1995 | Biedermann et al. |
| 5,466,237 A | 11/1995 | Byrd, III et al. |
| 5,474,551 A | 12/1995 | Finn et al. |
| 5,474,555 A | 12/1995 | Puno et al. |
| 5,476,464 A | 12/1995 | Metz-Stavenhagen et al. |
| 5,480,401 A | 1/1996 | Navas |
| 5,480,440 A | 1/1996 | Kambin |
| 5,499,983 A | 3/1996 | Hughes |
| 5,501,684 A | 3/1996 | Schlapfer et al. |
| 5,520,690 A | 5/1996 | Errico et al. |
| 5,531,746 A | 7/1996 | Errico et al. |
| 5,549,608 A | 8/1996 | Errico et al. |
| 5,554,157 A | 9/1996 | Errico et al. |
| 5,575,792 A | 11/1996 | Errico et al. |
| 5,578,033 A | 11/1996 | Errico et al. |
| 5,584,834 A | 12/1996 | Errico et al. |
| 5,586,984 A | 12/1996 | Errico et al. |
| 5,591,166 A | 1/1997 | Bernhardt et al. |
| 5,607,426 A | 3/1997 | Ralph et al. |
| 5,609,593 A | 3/1997 | Errico et al. |
| 5,647,873 A | 7/1997 | Errico et al. |
| 5,649,926 A | 7/1997 | Howland |
| 5,669,911 A | 9/1997 | Errico et al. |
| 5,672,176 A | 9/1997 | Biedermann et al. |
| 5,733,285 A | 3/1998 | Errico et al. |
| 5,733,286 A | 3/1998 | Errico et al. |
| 5,817,094 A | 10/1998 | Errico et al. |
| 5,876,403 A | 3/1999 | Shitoto |
| 5,882,350 A | 3/1999 | Ralph et al. |
| 5,885,286 A | 3/1999 | Sherman et al. |
| 5,951,553 A | 9/1999 | Betz et al. |
| 5,964,761 A | 10/1999 | Kambin |
| 5,964,988 A | 10/1999 | LaRose et al. |
| 6,022,350 A | 2/2000 | Ganem |
| 6,030,389 A | 2/2000 | Wagner et al. |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,090,110 A | 7/2000 | Metz-Stavenhagen |
| 6,090,111 A | 7/2000 | Nichols |
| 6,113,601 A | 9/2000 | Tatar |
| 6,280,442 B1 | 8/2001 | Barker et al. |
| 6,296,644 B1 | 10/2001 | Saurat et al. |
| 6,315,779 B1 | 11/2001 | Morrison et al. |
| 6,585,738 B1 | 7/2003 | Mangione et al. |
| 6,682,530 B2 | 1/2004 | Dixon et al. |
| 6,736,817 B2 | 5/2004 | Troxell et al. |
| 6,755,829 B1 | 6/2004 | Bono et al. |
| 6,858,031 B2 | 2/2005 | Morrison et al. |
| 6,884,241 B2 | 4/2005 | Bertranou et al. |
| 6,887,241 B1 | 5/2005 | McBride et al. |
| 7,220,262 B1 | 5/2007 | Hynes |
| 2002/0007183 A1 | 1/2002 | Lee et al. |
| 2002/0026194 A1 | 2/2002 | Morrison et al. |
| 2003/0032957 A1 | 2/2003 | McKinley |
| 2003/0105460 A1 | 6/2003 | Crandall et al. |
| 2003/0114853 A1 | 6/2003 | Burgess et al. |
| 2003/0135210 A1 | 7/2003 | Dixon et al. |
| 2004/0087949 A1 | 5/2004 | Bono et al. |
| 2004/0092931 A1 | 5/2004 | Taylor et al. |
| 2004/0127897 A1 | 7/2004 | Freid et al. |
| 2004/0225290 A1 | 11/2004 | Ferree |
| 2005/0038434 A1 | 2/2005 | Mathews |
| 2005/0049588 A1 | 3/2005 | Jackson |
| 2005/0113927 A1 | 5/2005 | Malek |
| 2005/0215999 A1 | 9/2005 | Birkmeyer et al. |
| 2005/0234451 A1 | 10/2005 | Markworth |
| 2005/0234452 A1 | 10/2005 | Malandain |
| 2006/0149237 A1 | 7/2006 | Markworth et al. |
| 2006/0149252 A1 | 7/2006 | Markworth et al. |

FOREIGN PATENT DOCUMENTS

| | | |
|---|---|---|
| FR | 2 780 631 | 1/2000 |
| WO | WO 00/54681 | 9/2000 |
| WO | WO 02/076315 | 10/2002 |
| WO | 2004/064603 | 8/2004 |
| WO | WO 2004/093701 | 11/2004 |

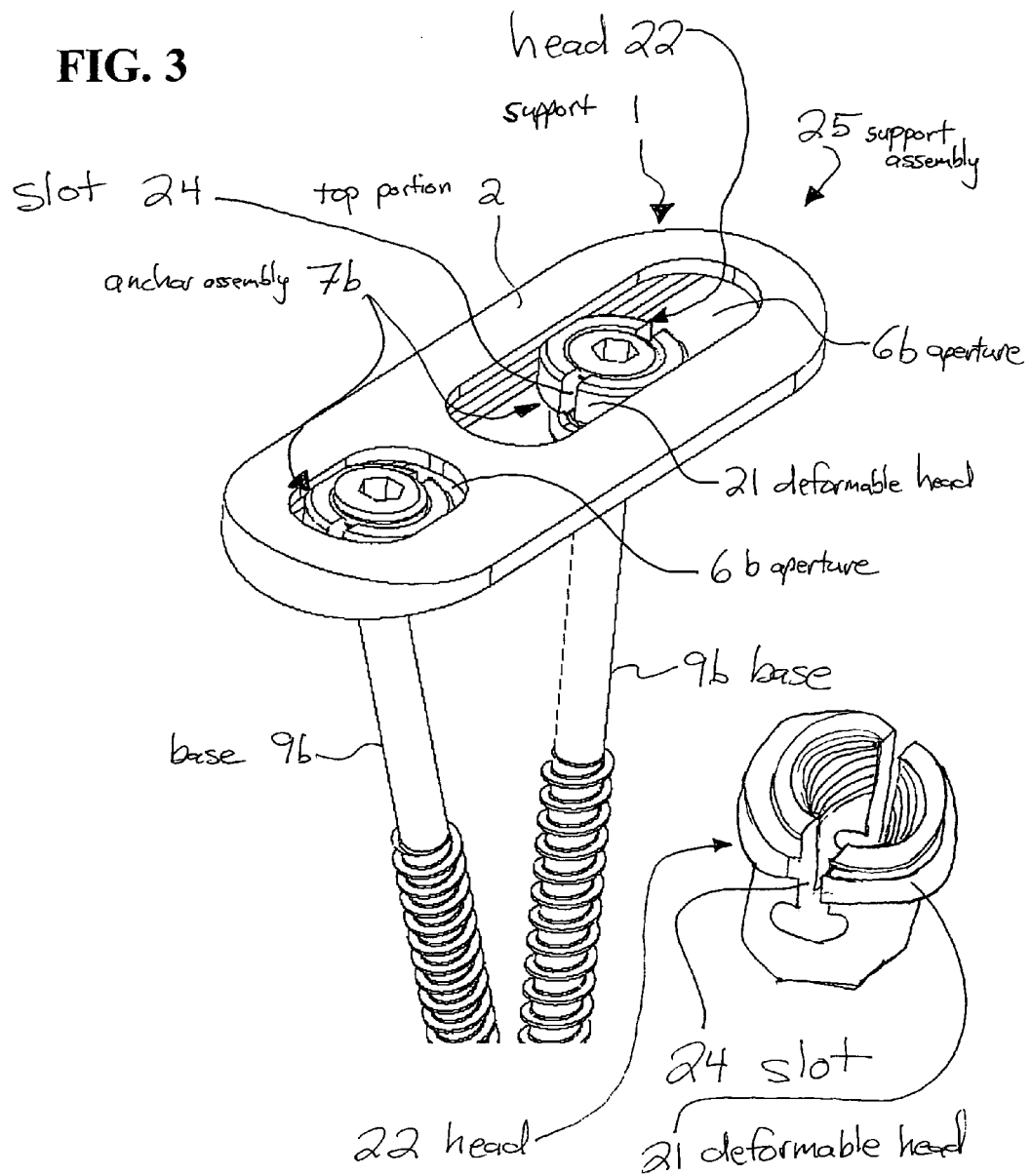

PLATE SYSTEM FOR MINIMALLY INVASIVE SUPPORT OF THE SPINE

This application is a continuation-in-part of and claims priority to U.S. patent application Ser. No. 10/826,684, filed Apr. 16, 2004 now U.S. Pat. No. 7,524,323, entitled "Subcutaneous Support", the disclosure of which is herein incorporated in its entirety by reference thereto.

TECHNICAL FIELD

This invention relates to medical devices.

BACKGROUND

The use of spinal stabilization/fixation devices to align position, and/or mechanically stabilize specific vertebrae or a region of the spine is well established. Typically such devices utilize a spinal fixation element, comprised of a relatively rigid member such as a plate, board or rod, which is used as a coupler between adjacent vertebrae. Such a spinal fixation element can effect a rigid positioning of adjacent vertebrae when attached to the pedicle portion of the vertebrae using pedicle bone anchorage screws. Once the coupled vertebrae are spatially fixed in position, procedures can be performed, healing can proceed or spinal fusion may take place.

Spinal fixation elements may be introduced posteriorly to stabilize the various vertebrae of the spine, for example, in conjunction with a kyphoplasty procedure wherein a void or cavity is made inside a vertebral body followed by filling with a bone substitute to form an "internal cast." Some conventional devices for this purpose are designed to be attached directly to the posterior of the spine, but the generally invasive nature of a conventional posterior approach used to implant these devices poses drawbacks. One minimally invasive solution to the problem of the posterior approach involves making a longitudinal separation of the sacrospinalis group between the multifudus and longissimus utilizing the natural cleavage plane between these two muscles rather than detaching the paraspinal muscles from the posterior spinal elements. Problems stemming from the prior art solutions include a high degree of invasiveness resulting in muscle disruption and blood loss. The loss of the paraspinal muscle attachment sites, formation of scar tissue, and loss of muscle function may compromise the patient's final outcome. Additionally, the prior art solutions are time consuming and are difficult to remove.

SUMMARY

In general, in one aspect, the invention features an implantable medical device for supporting a structure including a support having a top and bottom portion and one or more apertures passing therethrough. The bottom portion is adapted to receive a receiver. The receiver includes one or more anchor assemblies, each including a head and a base portion. The base portion engages the structure to be supported, and the receiver engages the bottom portion of the support. When the receiver is assembled with the support, the base does not pass through the one or more apertures. The receiver further includes a second anchor assembly passable through one of the apertures of the receiver and lockably engagable with the support.

Implementations of the invention can include one or more of the following features. The base can include a base head, wherein the base head is movably disposed within the anchor assembly. The base can further include a locking means for locking the base in a desired position relative to the support.

The one or more anchor assemblies of the device can be comprised of a means for locking the anchor assembly to the support.

The one or more apertures of the device can have a dimensional configuration providing access to a base and the means for locking an anchor assembly when assembled with the support.

The support of the device can have a shape selected from the group consisting of a board, plate, elongated cross-section, oval, square, I-beam and a rod. The support bottom portion can include a bottom surface, wherein the receiver is coupled to the bottom surface through a means including integral attachment and non-integral attachment.

The receiver and the anchor assembly of the device can be configured in an interconnecting geometry including a T-slot having a planar upper face, a planar lower face and a planar medial face. The receiver can include one or more access ports sized for coupling an anchor assembly to the receiver distally from the receiver ends.

The head of the one or more anchor assemblies and the second anchor assembly can include a slot, groove, track, dove tail and a snap-in configuration.

The base of the device can be a screw, staple, nail, hook or a pin. In one embodiment, the base is a screw that is a bone screw. The base head of the base can include a polyaxial and a hinge-type connector.

The means for locking the anchor assemblies to the support can include a deformable geometry of the head portion of the one or more anchor assemblies. The deformable geometry of the head can include a tapered void within the head, and a setscrew. Turning the setscrew into the threaded base aperture can result in deformation of the head outwardly, and thereby cause the head to engage the receiver to effect locking.

The means for locking the base can include a threaded base aperture and a setscrew. Turning the setscrew into the threaded base aperture can result in engagement of the base head to effect locking the base in a desired position.

The structure supported by the device can be a fractured bony structure.

In general, in another aspect, the invention features a method for supporting a bony structure. The method includes the steps of: 1) implanting one or more anchor assemblies having bases into bone; 2) connectively positioning a support having a receiver for the anchor assemblies on top of one or more of the anchor assemblies at a body location selected from the group including the subcutaneous fat layer of the back, muscle, cartilage and a bone; 3) locking the bases within one or more of the anchor assemblies; 4) locking one or more of the anchor assemblies within the support receiver; 5) passing through the support and implanting one or more additional anchor assemblies having bases into bone; 6) locking the bases within one or more of the additional anchor assemblies; and 7) locking one or more of the anchor assemblies within the support receiver. The bony structure that is supported can be fractured.

In general, in another aspect, the invention features a method for effecting a desired vertebral disc spacing including the steps of: 1) implanting a plurality of anchor assemblies having bases and a first and second locking means into vertebrae, wherein the bases of the anchor assemblies are unlocked for free movement; 2) interconnecting the anchor assemblies with the receiver of a support, wherein the anchor assemblies are unlocked within the receiver; 3) locking the bases within the anchor assemblies using the first locking means; 4) compressing or distracting the bases in relation to each other to achieve a parallel displacement of the instrumented vertebrae; and 5) locking the anchor assemblies within the support using the second locking means.

Aspects of the invention may include one of the following advantageous features. In various implementations of the invention wherein the support top portion has a smooth surface with no protruding features (e.g., screw heads or the like), such is desirable and advantageous since the smooth surface limits irritation of tissues and presents a smooth profile under the skin. In one implementation a smooth profile is achieved wherein the base head of the base, though accessible through the support, does not pass through the support or protrude above the top portion. In another implementation, a smooth profile is achieved wherein the support apertures are sized such that the anchor assembly can pass completely through the support top portion or bottom portion and be lockably engaged within the support without protruding from the support.

One non-standard implementation of the invention in relation to previous spinal fixation/stabilization devices, includes placement of the support in the subcutaneous fatty layer of the back. Such placement is desirable since less tissue irritation, discomfort and scarring will be experienced by a patient. Additionally, when a temporary support is indicated, such placement allows for easy removal of the support device once healing or treatment is complete (e.g., when a fractured or diseased vertebral body has been healed or treated).

Another non-standard implementation of the invention involves a two-step independent locking of the anchor assemblies to the support and of the bases to the anchor assemblies. The invention includes one type of anchor assembly constructed and arranged for loading and locking into a receiver by way of the bottom surface of the bottom portion of the support. These anchor assemblies include a first locking means for securing the anchor assembly within the support, and a second locking means for securing the base within the anchor assembly. In this implementation, the bases when loaded into the anchor assembly do not pass through the support, but can be accessed through an aperture in the support from above. Such an arrangement allows for a two-step independent locking process wherein either the anchor assembly is first locked to the support or the base is first locked to the anchor assembly. By selecting which feature is locked first, various procedures and maneuvers can be performed upon the structure(s) to which the bases are attached (e.g., manipulating vertebral body spacing, adjusting spinal curvature or both).

In certain implementations of the invention wherein three anchor assemblies having bases are provided, two anchor assemblies flanking a third central assembly can be manipulated to effect spacing and curvature of the spine and to hold the position of the spine around the spinal structure (e.g., vertebral body, annulus fibrosis or nucleus pulposus) to be treated. Correction maneuvers can be performed prior to, or after placement of, the central anchor assembly and base depending on the nature of the procedure to be performed. It should be understood that the spinal structure (vertebra or spinal disc) can be treated with or without the central anchor assembly in position, and with or without the support in position. If the support is in position, treatment can occur using instruments that pass through the aperture of the support. Treatment can also occur through the longitudinal aperture of any of the base(s). Another aspect of this implementation is the ease of insertion of the third anchor assembly through the top of the support. Additional surgical skill is required to align and attach a third anchor assembly in the receiver of the support, even more so than to align and attach two flanking anchor assemblies. In this implementation, the flanking anchor assemblies are positioned first in the receiver, and the central anchor assembly is positioned last and passes through the top of the support.

Methods using permutations and combinations of the two types of anchor assembly described herein are desirable for use in supporting structures. It is understood that a number of combinations of the two anchor assembly types including a support having two or three anchor assemblies are contemplated and are part of this disclosure. Included in the possible permutations of use are various alternative ordered steps for locking the anchor assemblies within the support and for locking the base within the anchor assembly.

In implementations of the invention wherein the anchor assembly includes a longitudinal aperture through the base and base head, the longitudinal aperture and setscrew aperture can be constructed and arranged for delivery of a bone substitute into the bone to be treated. Such an implementation allows for percutaneous placement of the base using imaging guidance such as fluoroscopy, and for delivery of bone filler material.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 is a drawing of the device showing two anchor assemblies positioned within the support.

Like reference symbols in the various drawings indicate like elements.

DETAILED DESCRIPTION

As shown in FIGS. 1A-E, FIG. 2 and FIG. 3, a support 1 is provided having a shape. The support 1 preferably is elongate and of a sufficient length to span a number of vertebrae in the spine. The support 1 shape can include board, elongated cross-section, rod, oval, square, and I-beam, as the needs of the patient's anatomy and/or mechanical requirements dictate. The length of the support 1 is minimally substantially the same length as required to span two or more vertebrae. In one implementation, the support 1 is substantially a length as required to span three vertebrae. In another implementation, the length of the support 1 is substantially between 25 to 140 millimeters. The support 1 can be made of materials that are durable and that can be implanted in a body, including titanium, stainless steel, carbon fiber, etc. In one implementation, the support 1 is made of titanium. In another implementation the support 1 is made of a biocompatible material, a reabsorbable material or a combination of any of the foregoing materials and/or alloys thereof. In use, the support 1 and attending anchor assemblies 7 (described in detail below) can be used for temporary or permanent implantation, with the degree of permanence determined post facto.

Figure 1A:
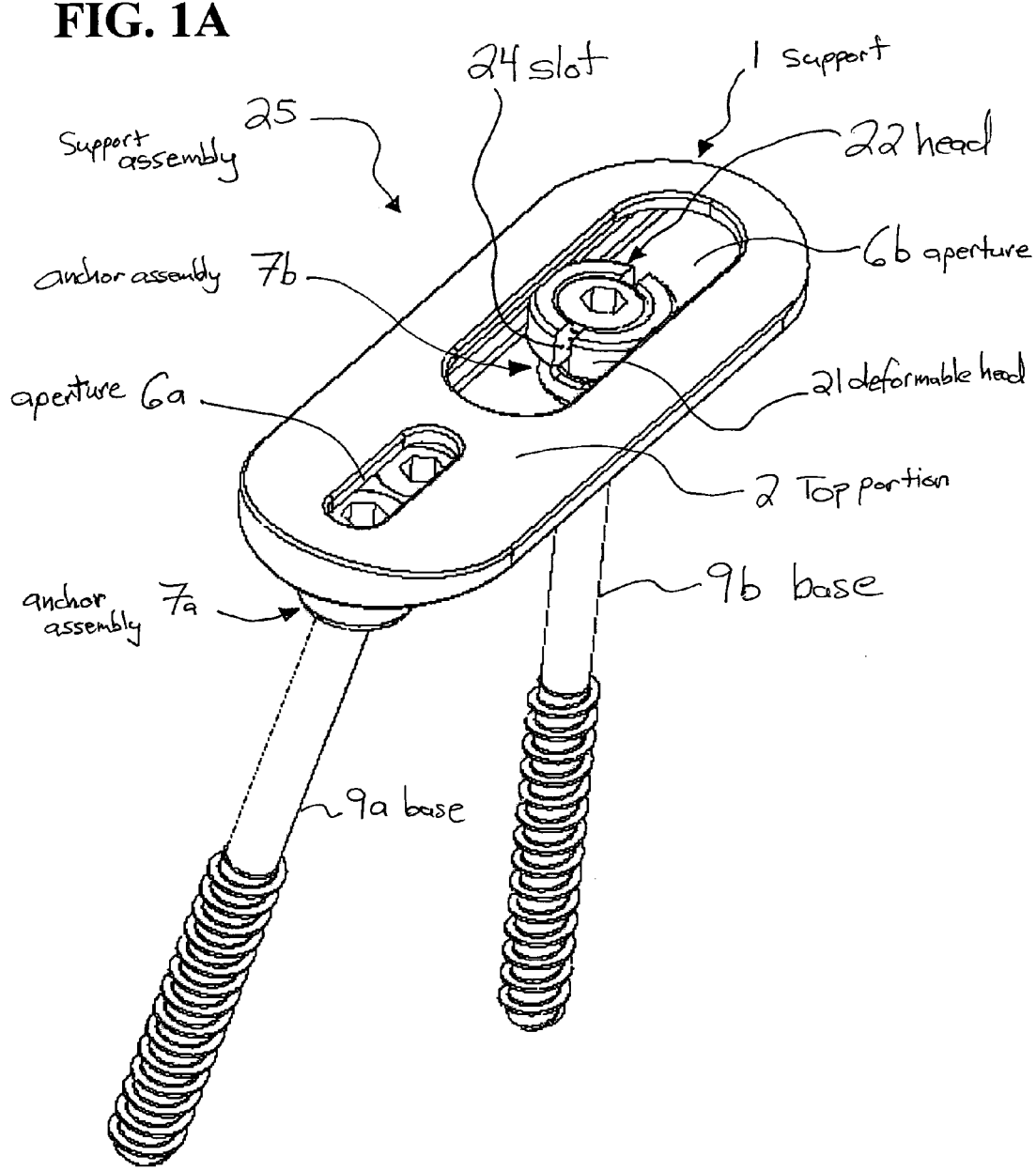
FIG. 1A is a drawing of a support device showing two different anchor assembly types positioned within the support.
Figure 1B:
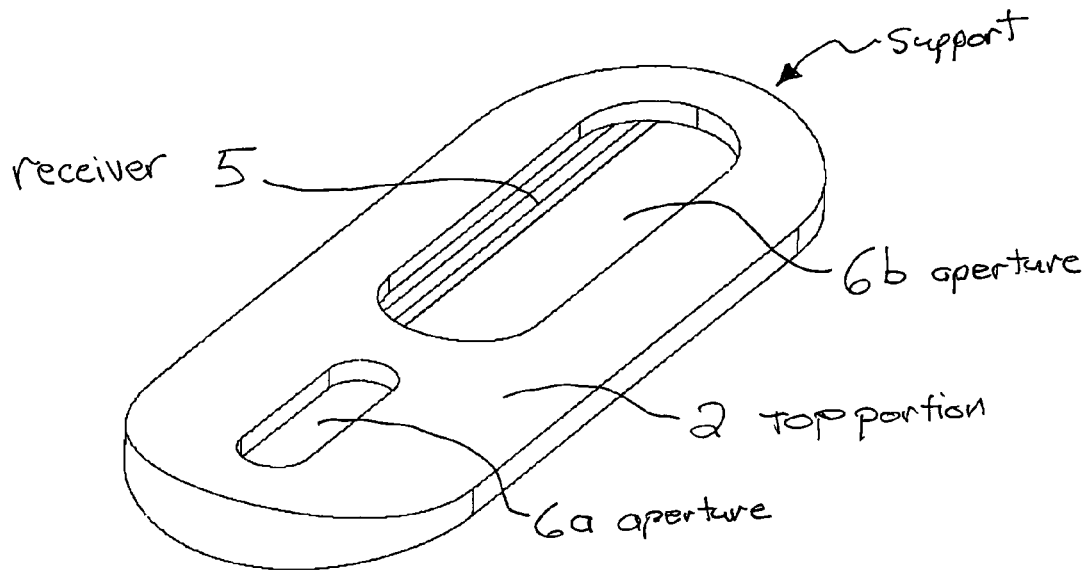
FIG. 1B is a drawing showing a top view of the support, illustrating the receiver and apertures.
Figure 1C:
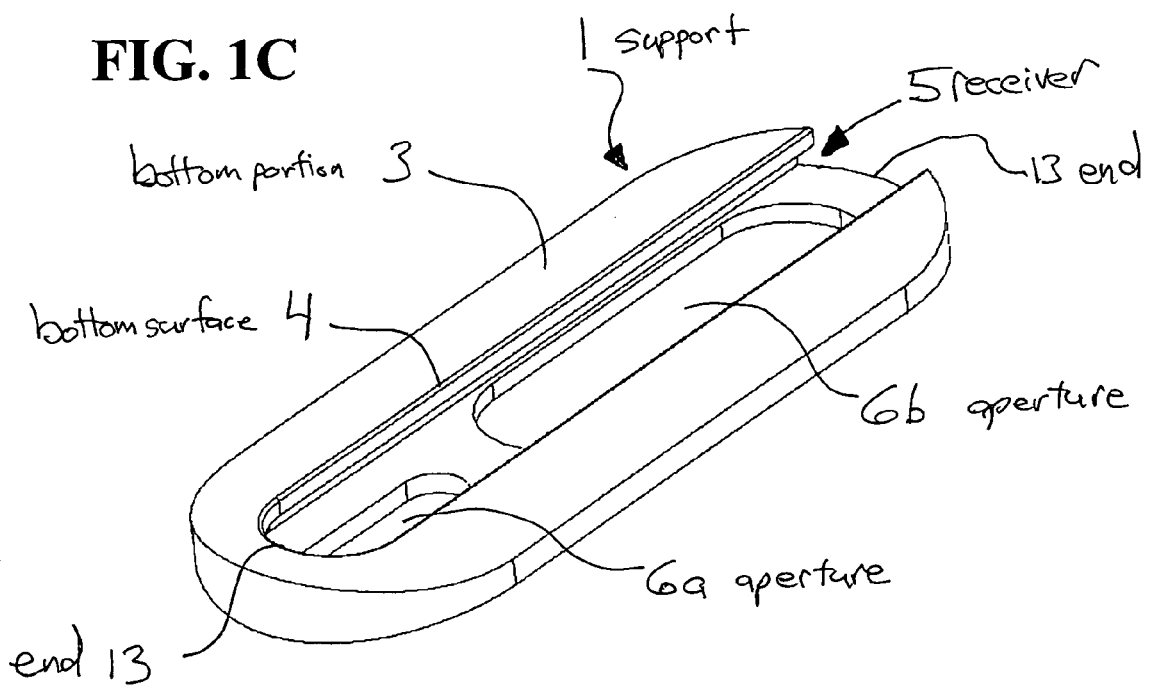
FIG. 1C is a drawing showing a bottom view of the support, illustrating the receiver and apertures.

As shown in FIGS. 1B and 1C, the support 1 includes a top portion 2 and a bottom portion 3 having a bottom surface 4 and a receiver 5. Additionally, as shown in FIGS. 1A-D, FIG. 2, and FIG. 3, the support 1 can include a number of centrally aligned apertures 6. The apertures 6 may also be offset or staggered. The apertures 6 can have any of a number of shapes not limited to openings having a round, oval, scalloped or elongate shape. Any number of apertures 6 can be employed, including one or more. In use (i.e., assembled with a plurality of anchor assemblies 7) the support 1 top portion 2 can have a smooth surface with no protruding features (e.g., screw heads or the like).

In one implementation, two apertures 6 per support 1 are included (see FIGS. 1A-D). In another implementation, three apertures 6 per support 1 are included (see FIG. 2). Any type of spacing of apertures 6 can be used, including even or staggered. In one implementation, the apertures 6 are spaced evenly and separated by a distance substantially equivalent to the spacing of the vertebrae of a spine. Alternatively, the apertures 6 can be spaced closer together than the spacing of vertebrae of a spine. The spacing of the apertures may also be determined by the type of bone to be treated, for example long bones such as the femur. In one implementation, the aperture(s) 6 are sized for and limited to a size sufficient for accessing the features of the anchor assembly 7 (described in detail below) with a tool or object through the top portion 2 of the support element 1 (e.g. to engage the locking means of the anchor assembly 7 using, for example, a hex-headed screw driver). In this way, as shown in FIG. 1A and FIG. 2, when the support 1 and the anchor assembly 7 are assembled, the base head 8 of the base 9 (both described in detail below), though accessible through the support 1, does not pass through the support 1.

In another implementation, the aperture(s) 6a are sized such that when the support 1 and the anchor assembly 7a are assembled, the base head 8 portion of the base 9 can engage the support 1 (e.g., from beneath), but the base 9 does not pass through the support 1.

In another implementation, the aperture(s) 6b are sized such that the anchor assembly 7b can pass completely through the support 1 top portion 2 or bottom portion 3, such that the anchor assembly 7b can be lockably engaged within the support 1 as desired.

Figure 1D:
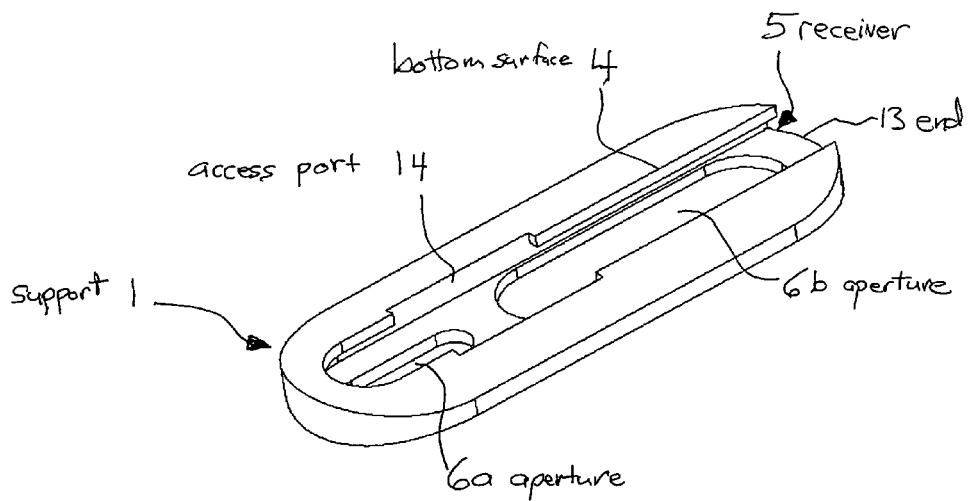
FIG. 1D is a drawing showing a bottom view of the support, illustrating the anchor assembly access ports.
Figure 1E:
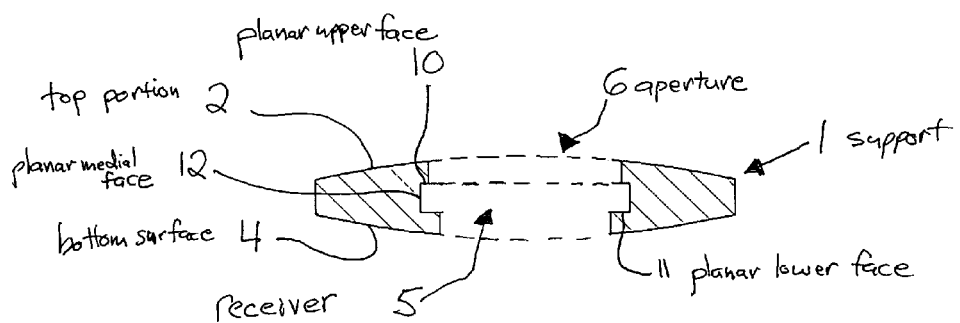
FIG. 1E is a drawing showing a cross-sectional end view of the support, illustrating the receiver.
Figure 2:
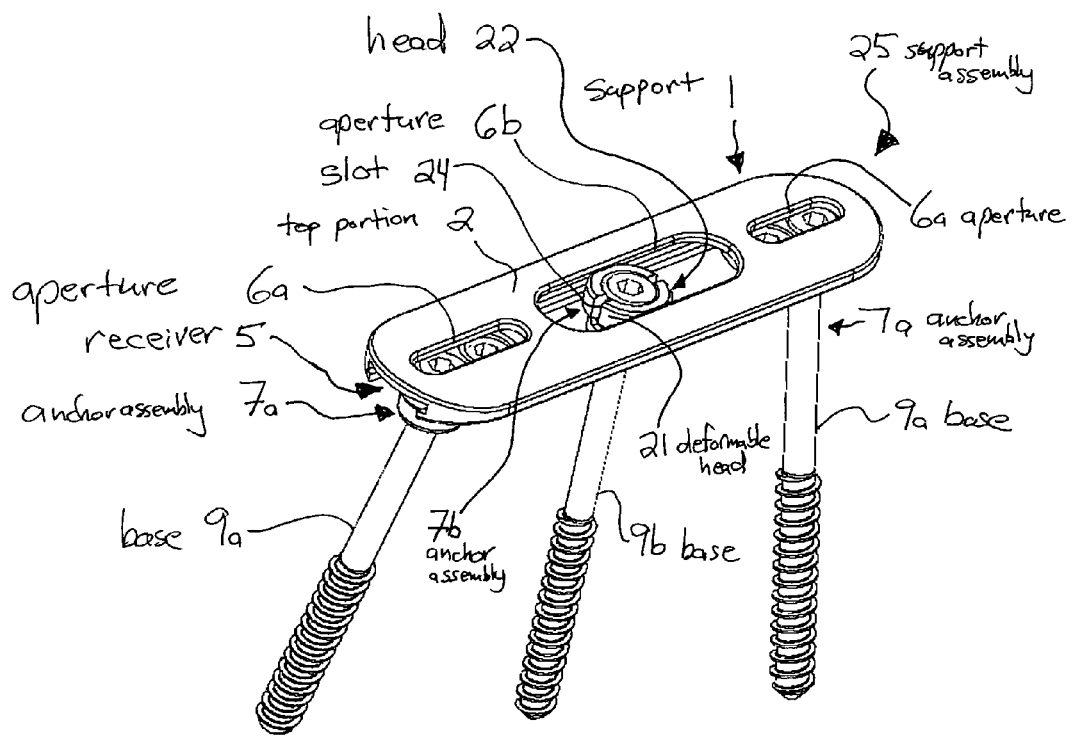
FIG. 2 is a drawing of the device showing three anchor assemblies positioned within the support.

As shown in FIGS. 1B-E, the support 1 includes a receiver 5 that can be integrally disposed within the bottom surface 4 of the support 1. Alternatively, the receiver 5 can be coupled to the bottom surface 4 of the support 1 (for example, a track-type receiver 5 can be attached by rivets, screws or other attachment means, to the bottom surface 4 of the support 1). The receiver 5 can be configured as a slot, groove, track, dovetail, one-way snap-in design, or the like. In one implementation, the receiver 5 is configured in a twist-in configuration, wherein the anchor assembly 7 has two dimensions. The first dimension allows the anchor assembly 7 to pass into the receiver 5 (not shown). As the base head 8 is rotated 90 degrees with respect to the receiver 5 and, upon completing the 90-degree rotation, the second dimension maintains the base 9 in the receiver 5. In another implementation, as shown in FIGS. 1B-C and 1E, the receiver 5 is a T-slot configuration. As shown in FIG. 1E, in cross-section, the receiver 5 includes a planar upper face 10, a planar lower face 11 and a planar medial face 12. Alternatively, where the configuration of the receiver 5 is a dovetail, the receiver 5 includes a planar upper face 10 and an angled face (not shown). In yet another alternative, where the receiver 5 is of a curved or rounded shape, the receiver 5 includes a curved or rounded receiver 5 face (not shown). The receiver 5 can span all or part of the length of the bottom surface 4 of the support 1. As shown in FIGS. 1C and 1D, each end 13 of the receiver 5 can be open or closed. In one implementation, both ends 13 of the receiver 5 are open (not shown). In another implementation, one end 13 of the receiver 5 is open and the opposite end 13 is closed (see FIGS. 1C and 1D). In another implementation, both ends 13 of the receiver 5 are closed (not shown).

As shown in FIG. 1D, the receiver 5 can include anchor assembly access ports 14 that provide openings in the pathway of the receiver 5, whereby the anchor assemblies 7 can be interconnected to the support 1 without having to traverse the length of the receiver 5 when accommodating multiple (or even a single) anchor assemblies 7. The anchor assembly access ports 14 can be of a sufficient size to accept the anchor assembly 7 and can be spaced evenly, or staggered as desired. The anchor assembly access ports 14 also allow assembly when the ends 13 of the receiver 5 are closed.

Figure 4A:
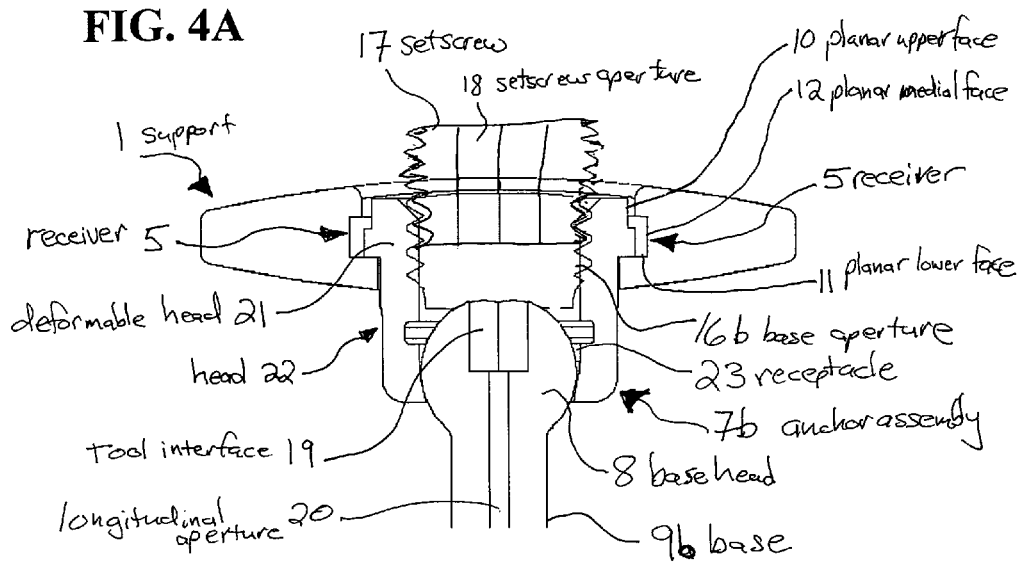
FIG. 4A is a drawing showing a cutaway view of one anchor assembly type and the support, illustrating the receiver of the support, and the anchor assembly prior to locking into the support.
Figure 4B:
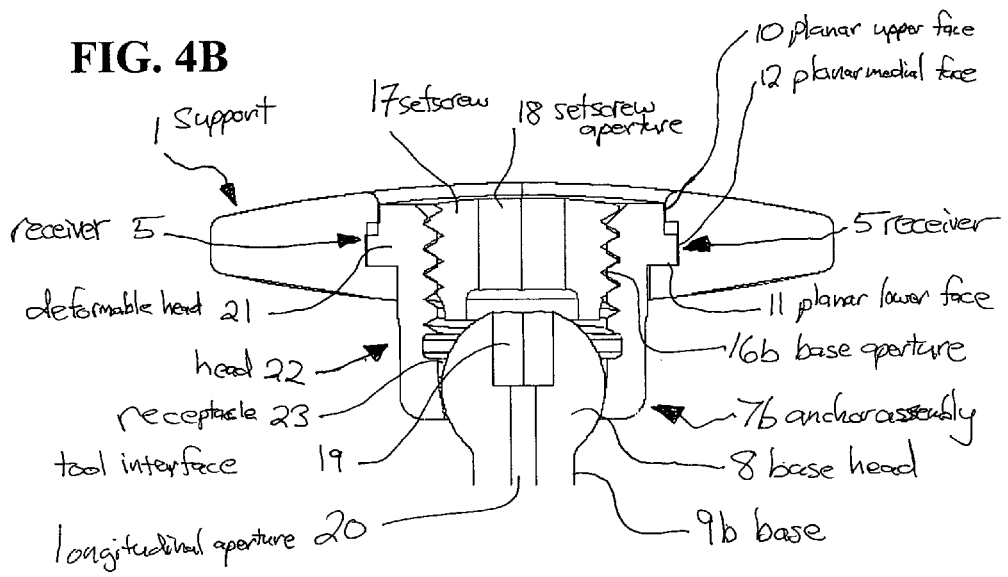
FIG. 4B is a drawing showing a cutaway view of one anchor assembly type and the support, illustrating the receiver of the support, and the anchor assembly after locking into the support.
Figure 5:
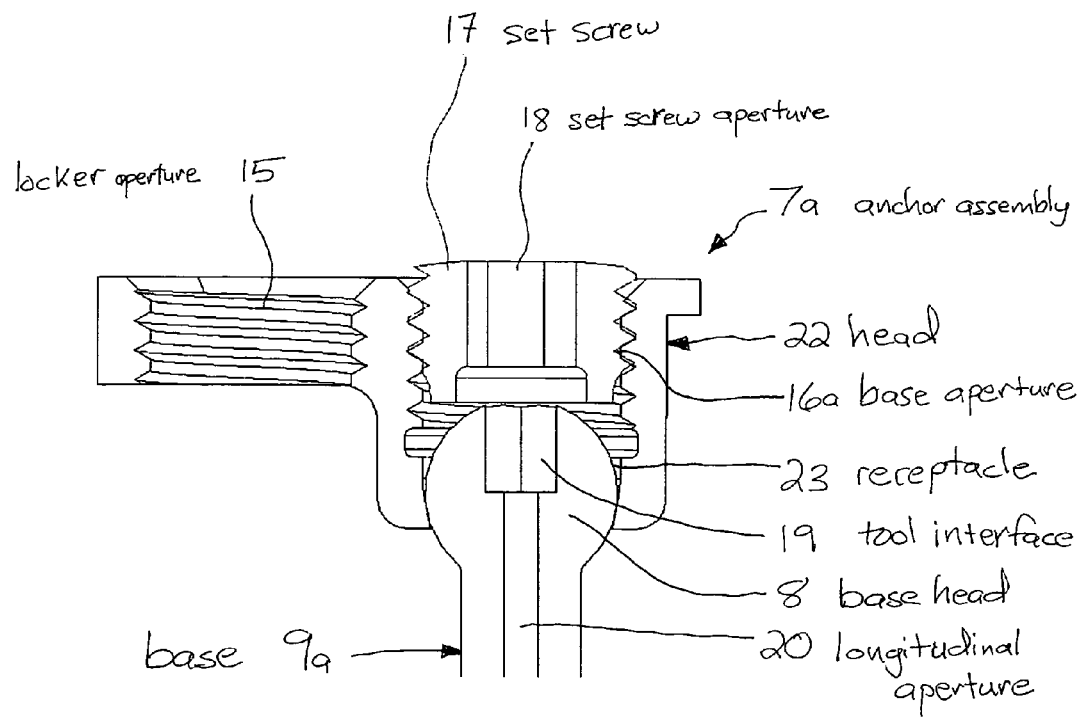
FIG. 5 is a drawing showing a cutaway view of another anchor assembly type, illustrating the anchor assembly head, base, base head, longitudinal aperture, tool interface, receptacle, base aperture and setscrew.

As shown in FIGS. 4A and 4B, the anchor assembly 7b is configured to interconnect with the shape of the receiver 5. As described above for the receiver 5, the anchor assembly 7 forms a complimentary shape, which can be any of a number of shapes. In some implementations, the mating between the support 1 and the anchor assembly 7 occurs only in two dimensions (e.g. where a 90 degree twisting receiver 5 is employed). As shown in FIGS. 4A-B and FIG. 5, the anchor assembly 7b can be comprised of a head 22, a base 9b and a base head 8. The anchor assembly 7b can be comprised of numerous materials that are durable and that can be implanted in a body, including titanium, stainless steel, carbon fiber, etc. Additionally, the anchor assembly 7b can be comprised of a reabsorbable material or a biocompatible material, or a combination of any of the foregoing materials.

As shown in FIGS. 4A-*and* 4B, the anchor assembly 7b includes a means for locking the anchor assembly 7b to the support 1. In one implementation, as shown in FIG. 4A, where the receiver 5 and complimentary head 22 of the anchor assembly 7b are T-slot shaped, the means for locking the anchor assembly 7b can be a setscrew 17 threaded into the head 22 of the anchor assembly 7b, wherein the head 22 includes a threaded base aperture 16b and a deformable geometry. As shown in FIG. 4B, when the setscrew 17 is turned into the threaded base aperture 16b, the deformable head 22 is caused to splay outward such that the T-slot shape of the head 22 engages and locks against the receiver 5 planar medial face 12. Alternatively, the head 22 may additionally engage the receiver 5 planar upper face 10 or planar lower face 11 or both to effect locking. In one implementation, the means for locking the anchor assembly 7b is constructed and arranged such that a first step of turning the setscrew 17 into the threaded base aperture 16b results in engagement and tightening of the base head 8 within the anchor assembly receptacle 23 in a desired position. In this implementation, the means for locking is further constructed and arranged such that a second step of further turning the setscrew 17 results in an outward splaying of the deformable head 22, resulting in locking the anchor assembly 7*b* within the receiver 5 as discussed above. In another implementation, a cam can be substituted for the setscrew 17 to effect the locking of the anchor assembly 7*b* within the support 1 (not shown).

The deformable geometry of the deformable threaded base aperture 16*b* can be comprised of a void within the anchor assembly 7*b* head 22 wherein the void is selected from the list consisting of a cavity, slot notch, groove, cut out, gap and a recess. In one implementation, the void is tapered. In another implementation as shown in FIG. 1A, FIG. 2, and FIG. 3, the void within the anchor assembly 7*b* head 22, can be a slot 24 cut into the head 22 (see detail in FIG. 3).

As shown in FIG. 5, the anchor assembly 7*a* includes an alternative means for locking the anchor assembly 7*a* to the support 1. In one implementation, where the receiver 5 and complimentary anchor assembly 7*a* are T-slot shaped, the means for locking the anchor assembly 7*a* can be a setscrew 17 disposed within a threaded anchor assembly 7*a* locker aperture 15 (see FIG. 5); wherein turning the setscrew 17 causes the setscrew 17 to move toward the top portion 2 of the support 1, where the setscrew 17 engages the receiver 5 planar upper face 10 (not shown). When the setscrew 17 engages the receiver 5, the anchor assembly 7*a* presses against the receiver 5 planar lower face 11 to effect locking (see FIG. 1E). Alternatively, a cam can be substituted for the setscrew 17 to effect the locking of the anchor assembly 7*a* within the support 1.

In other implementations where the receiver 5 and complimentary anchor assembly 7 are of alternative shapes or configurations (e.g. dove tail or rounded), means analogous to those discussed above for locking an anchor assembly to the support are provided.

Other means for locking an anchor assembly 7 to the support 1 are envisioned, including means as disclosed in U.S. application Ser. No. 10/826,684, filed Apr. 16, 2004, entitled "Subcutaneous Support", which is incorporated herein by reference in its entirety.

As shown in FIGS. 4A-B and FIG. 5, the anchor assembly 7 includes a base 9 moveably disposed within the threaded base aperture 16. The base 9 can be a screw, staple, hook or nail and of a type typically used for anchoring to a structure (e.g., to a bone). In one implementation, the base 9 is a screw of a type for insertion into the pedicle of a vertebra. In another implementation, the base can be attached to another bony structure.

Attachment of the base 9 to the anchor assembly 7 can be made in any of a number of ways. In one implementation, the attachment is through a hinge-type of connection between the base 9 and the anchor assembly 7 (not shown). In another implementation, as shown in FIGS. 4A-B and FIG. 5, the attachment is made between a polyaxial-type base head 8 on the base 9 and a complimentary receptacle 23 within the anchor assembly 7 head 22.

The anchor assembly 7 further includes a means for locking the base 9 within the anchor assembly 7 head 22. As shown in FIGS. 4A-B and FIG. 5, for a polyaxial-type base head 8, the means for locking can include a setscrew 17 disposed within a threaded base aperture 16. In this configuration, turning the setscrew 17 causes the setscrew 17 to press directly against the polyaxial base head 8 of the base 9, thereby forcing the polyaxial base head 8 against the receptacle 23 of the anchor assembly 7 to effect locking. Alternatively, where the base 9 is of the hinge-type, the means for locking could be comprised of a setscrew 17 disposed in a threaded base aperture 16. In this configuration, turning the setscrew 17 causes the setscrew 17 to press directly against the base head 8 of the hinge-type base 9, thereby creating friction against the hinge's pin to effect locking (not shown). In another implementation, a cam can be substituted for the setscrew 17 to effect locking (not shown).

As shown in FIGS. 4A-B and FIG. 5, another implementation of the anchor assembly 7 includes a longitudinal aperture 20 through the base 9 and base head 8, a tool interface 19 and a setscrew aperture 18. The longitudinal aperture 20 and setscrew aperture 18 are configured such that an instrument, wire (e.g. a K-wire) or other guide can pass through the entire anchor assembly 7. The longitudinal aperture 20 and setscrew aperture 18 can also be configured for delivery of a bone substitute into the bone to be treated. The setscrew aperture 18 is further configured such that a tool or instrument can pass through the setscrew aperture 18 to engage the tool interface 19 of the base 9. Alternatively, the setscrew 17 can be a cam (not shown).

The setscrew aperture 18 can be any shape and can be sized to accommodate the through passage and use of objects and tools without affecting the positioning of the setscrew. The setscrew aperture 18 and longitudinal aperture 20 can also be sized and configured to allow passage of instruments (for example, expandable structures, bone cutting or scraping tools, tools for delivery of bone substitute materials) used for treating and fixing a fracture of the bone, such as in a kyphoplasty procedure.

The longitudinal aperture 20 can have any desired cross-sectional shape including but not limited to round, square, hexagonal, oval or any regular or irregular shape.

The tool interface 19 can be any shape suitable for receiving a tool for manipulating the base 9. For example, where the base 9 is a screw, the tool interface 19 can be a hex shape, or any other commonly used screw head tool interface shape.

Where an anchor assembly 7 has the above configuration, the setscrew 17 can be pre-positioned within the base aperture 16 without being tightened. The setscrew aperture 18 and longitudinal aperture 20 (passing through the base 9 and base head 8) enable access through a pre-assembled implementation of the anchor assembly 7. Additionally, wherein the anchor assembly 7 is pre-assembled, access is provided to the tool interface 19 of the base head 8 through the setscrew aperture 18.

A method of using an anchor assembly 7 having the above configuration to secure the anchor assembly 7 into a structure (e.g. into a bone, such as a vertebra) can include the steps of: 1) positioning a K-wire at the target site; 2) passing the anchor assembly 7 onto the K-wire and guiding the anchor assembly 7 down the K-wire length to the target site; 3) engaging the tool interface 19 of the base 9 by passing through the setscrew aperture 18 with a tool; 4) securing the base 9 into the structure at the target site using the tool (e.g. by screwing into vertebrae), 5) withdrawing the tool from the tool interface 19; and 6) securing the base 9 or support 1 to the anchor assembly 7 using the setscrew 17. Optionally, the method can include treating the structure to be secured.

The support 1 and one or more anchor assemblies 7, once assembled, can be used to support a bony structure. When mated, the support 1 and one or more anchor assemblies 7 form a support assembly 25 (see FIG. 1A, FIG. 2 and FIG. 3). The bony structure supported can include a femur or other bones of the leg (e.g. tibia and fibula), bones of the arm and wrist (e.g. humerus, radius and ulna), and other bones such as the calcaneus, pelvis, spine and the like. Support can be provided for a single bone (i.e. a long bone such as the femur, tibia, humerus) or for more than one bone (i.e. vertebrae).

In use, the support assembly 25 can support a bony structure wherein the support 1 is disposed within a body location including the subcutaneous fat layer of the back, muscle, cartilage, bone and the like. Alternatively, the support 1 is disposed adjacent to bone. In another implementation, the support 1 is disposed external to the body.

Additionally, the support assembly 25 includes a freedom of movement with regard to the base 9 within the anchor assembly 7 and the anchor assembly 7 within the support 1. That is, prior to locking respective base 9 and the anchor assembly 7 elements of the support assembly 25 (hereinafter referred to as an unlocked configuration), the elements of the support assembly 25 are movable and have one or more degrees of freedom so as to allow for movement of the underlying structure being supported. For example, in the unlocked configuration, the support assembly 25 is configurable so as to facilitate manipulation of vertebral spacing and/or curvature correction.

As shown in FIG. 1A, FIG. 2 and FIG. 3, several implementations of the support assembly 25 can be useful to effect an increase or decrease the vertebral disc space/height, or to increase or decrease the amount or lordotic/kyphotic curve of the spine, also called curvatures of the spine. Manipulation of vertebral disc spacing and spine curvature can be achieved with each of the implementations shown.

As shown in FIG. 1A, one implementation of support assembly 25 includes a support 1 with a first and a second anchor assembly 7. In this implementation the first anchor assembly 7a includes independent base 9 -to-anchor assembly 7 and anchor assembly 7 -to-support 1 locking means, and is configured such that when assembled with the support 1, the base 9a does not pass through the aperture 6a. In contrast, the second anchor assembly 7b is configured for substantially concurrent base 9 and anchor assembly 7 locking and is configured to be passable through the support 1. As shown in FIGS. 1A-E, the sizing of the aperture 6, determines whether a first or second anchor assembly 7 variant (7a or 7b) can be accommodated.

As shown in FIG. 2, in another implementation, an additional first anchor assembly 7a, can be arranged such that the second anchor assembly 7b is flanked by two first anchor assemblies 7a. In use, this arrangement as shown in FIG. 2, can provide attachment to and manipulation of three consecutive vertebrae. For example, the flanking first anchor assemblies 7a could be attached to two individual vertebrae that flank a third vertebrae to which the second anchor assembly 7b could be attached.

As shown in FIG. 3, in another implementation, the support assembly 25 can include two anchor assemblies 7b configured for substantially concurrent base 9 and anchor assembly 7 locking and configured to be passable through the support 1.

A method of use of the invention for effecting a desired vertebral disc spacing, can include the steps of: 1) implanting the bases 9 of a plurality of anchor assemblies 7 into vertebrae, wherein the bases 9 of the anchor assemblies 7 are unlocked within the anchor assemblies 7 for free movement of the head 22; 2) interconnecting the anchor assemblies 7 with the receiver 5 of the support 1, wherein the anchor assemblies 7 are unlocked within the receiver 5; 3) locking the bases 9 within the anchor assemblies 7 (e.g. using a setscrew 17 or cam); 4) compressing or distracting the bases 9 in relation to each other (e.g. to achieve a parallel displacement of the instrumented vertebrae); and 5) locking the anchor assemblies 7 within the support 1 (e.g. using a set screw 17 or cam).

"Instrumented" meaning where a physical connection exists between a structure (e.g. a vertebra) and a medical device or instrument.

A method of use of the invention for effecting a desired curvature of the spine can include the steps of: 1) implanting the bases 9 of a plurality of anchor assemblies 7 into vertebrae, wherein the bases 9 of the anchor assemblies 7 are unlocked within the anchor assemblies 7 for free movement of the head 22; 2) interconnecting the anchor assemblies 7 with the receiver 5 of the support 1, wherein the anchor assemblies 7 are unlocked within the receiver 5; 3) compressing or distracting the anchor assemblies 7 in relation to each other (e.g. to affect the lordotic/kyphotic curvature of the spine); 4) locking the bases 9 within the anchor assemblies 7 and locking the anchor assemblies 7 within the support 1 (e.g. using a setscrew 17 or cam).

Another method of using the invention to support the spine can include the steps of: 1) setting a series of anchor assemblies 7 percutaneously in place along the spine through a series of small incisions including screwing a bone anchorage screw of each anchor assembly 7 into one or more adjacent pedicle portions of adjacent vertebrae in the spine, such that the anchor assemblies' receiver 5 mating parts align in a parallel plane within the subcutaneous fat layer of the back; 2) loading the support 1 on top of the anchor assemblies 7 including engaging the mated parts of the receiver 5 and the anchor assembly 7, either by sliding, snapping or otherwise positioning the support 1 into the desired position; 3) accessing and locking the anchor assembly 7 in the support 1 using the locking means of the anchor assembly 7 via the support 1 apertures 6; and 4) optionally locking the base 9 of the anchor assembly 7 using the locking means (e.g. setscrew 17 or a cam) for the bone anchorage screw via the support 1 apertures 6.

Other methods of using the invention to support the spine can include a variety of combinations of the two types of anchor assembly (7a and 7b) described herein and shown in FIG. 1A, FIG. 2 and FIG. 3. A number of combinations of the two types of anchor assembly 7 including a support 1 having two or three anchor assemblies 7 attachable thereto can be used to support the spine. For example, the support assembly 25 could include two anchor assemblies 7a, or two anchor assemblies 7b (as shown in FIG. 3), or one anchor assembly 7a and one anchor assembly 7b (as shown in FIG. 1A). Alternatively, the support assembly 25 could include three anchor assemblies 7 consisting of two anchor assemblies 7a and one anchor assembly 7b arranged in the support in any possible substantially linear order. An example of one such arrangement is shown in FIG. 2. Alternatively, the support assembly 25 could include three anchor assemblies 7 consisting of two anchor assemblies 7b and one anchor assembly 7a arranged in the support in any possible substantially linear order (not shown).

Additional permutations for using the invention include employing various alternatively ordered steps for locking anchor assemblies 7 within the support 1 and for locking the base 9 within the anchor assembly 7. For example, a given anchor assembly 7a can be locked in position within the support 1 in a first step, followed by locking of the base 9 within the anchor assembly 7a or vice versa.

The method of supporting the spine can also be used in conjunction with a kyphoplasty procedure. Kyphoplasty is a percutaneous technique involving the use of an expandable structure, such as a balloon catheter, to create a cavity or void within the vertebral body, followed by filling the cavity with a bone substitute to form an "internal cast". The bone substitute could be any appropriate filling material used in orthopedic surgery, including but not limited to, allograft or autograft tissue, hydroxyapatite, epoxy, PMMA bone cement or synthetic bone substitutes, medical grade plaster of Paris or calcium phosphate or calcium sulfate cements. Methods and instruments suitable for such treatment are more fully described in U.S. Pat. Nos. 4,969,888 and 5,108,404, which are incorporated herein by reference. Kyphoplasty can be used to reduce vertebral compression fractures and to move bone with precision, thus restoring as close to normal the pre-fracture anatomy of the vertebral body. Vertebral compression fractures caused by trauma (for example, due to automobile accidents or falls), have traditionally been treated with open reduction, internal fixation stabilization hardware and fusion techniques using a posterior approach. The stabilization hardware is used to offload the fractured vertebral body and to stop motion across the disc so that bone graft can fuse one vertebra to the next and the stabilization hardware usually becomes a permanent implant. In trauma, the stabilization hardware may be designed to facilitate easy removal after fusion has occurred. Stabilization hardware can take many forms, including those described herein.

The combination of kyphoplasty and insertion of stabilization hardware utilizing the naturally occurring interior muscle plane as described in Wiltse and Spencer, Spine (1988) 13(6):696-706, satisfies the goals of improving the quality of patient care through minimally invasive surgical therapy.

A number of preferred embodiments of the invention have been described. Nevertheless, it will be understood that various modifications may be made without departing from the spirit and scope of the invention. For example, while the some implementations have been described using screws to anchor into bony structures, the scope of the invention is not so limited. Any means of anchoring can be used, such as a cam, screw, staple, nail, pin, or hook. Accordingly, other embodiments are within the scope of the following claims.

What is claimed is:

1. An implantable medical device for supporting a structure comprising:
    a support having a top surface and bottom portion and one or more apertures passing therethrough, the bottom portion including a bottom surface and a receiver;
    the receiver including one or more anchor assemblies, each of the one or more anchor assemblies including a deformable head and a base portion movably supported by the deformable head, the base portion extending from the bottom surface for engaging with the structure to be supported, the deformable head engaging with the receiver of the support, each of the anchor assemblies further including means for locking the anchor assembly passable through the top surface of said support and the one or more apertures to engage and deform the deformable head into locking engagement with the receiver of the support; and
    a second anchor assembly lockably engagable with the support;
    wherein the base portion includes:
    a base head,
    wherein the base head is movably disposed within the deformable head, and the means for locking the anchor assembly further locks the base head in the deformable head in a desired position relative to the support
    wherein the deformable head includes a receptacle and the base head is supported relative to the support in the receptacle, the deformable head further including an aperture extending from the receptacle toward the top surface of the support for receiving the means for locking the anchor assembly through the one or more apertures of the support.

2. The implantable medical device of claim 1, wherein the one or more apertures and the deformable head have a configuration providing access to the base portion in the deformable head.

3. The implantable medical device of claim 1, wherein the support has a shape selected from the group consisting of a board, plate, elongated cross-section, oval, square, I-beam and a rod.

4. The implantable medical device of claim 1, wherein the receiver is coupled to the bottom surface through a means selected from the group consisting of integral attachment and non-integral attachment.

5. The implantable medical device of claim 1, wherein the receiver and the anchor assembly are configured in an interconnecting geometry comprising a T-slot having a planar upper face, a planar lower face and a planar medial face.

6. The implantable medical device of claim 1, wherein the receiver is comprised of one or more access ports sized for coupling an anchor assembly to the receiver distally from the receiver ends.

7. The implantable medical device of claim 1, wherein the deformable head of the one or more anchor assemblies includes a configuration selected from the group consisting of a slot, groove, track, dove tail and a snap-in configuration.

8. The implantable medical device of claim 1, wherein the base portion is one of a screw, staple, nail, hook and a pin.

9. The implantable medical device of claim 1, wherein the base portion is a bone screw.

10. The implantable medical device of claim 1, wherein the base head forms one of a polyaxial and a hinge-type connection with the deformable head.

11. The implantable medical device of claim 1, wherein the means for locking the anchor assembly to the support includes a set screw an the aperture of the deformable head is threaded for receiving the set screw.

12. The implantable medical device of claim 11, wherein the threaded aperture of the deformable head is comprised of a tapered void within the deformable head,
    wherein turning the setscrew into the threaded aperture results in deformation of the deformable head outwardly into engagement with the receiver to lockingly engage the anchor assembly to the support.

13. The implantable medical device of claim 1, wherein the base portion is connected with the deformable head via one of a polyaxial and a hinge-type connection.

14. The implantable medical device of claim 1, wherein the means for locking the anchor assembly is comprised of a threaded base aperture in the deformable head and a setscrew positionable into the threaded base aperture, wherein turning the setscrew into the threaded base aperture splays the deformable head outwardly into locking engagement with the receiver.

15. The implantable medical device of claim 14, wherein the receiver includes a planar medial face extending between a planar upper face and a planar lower face, and the deformable head engages at least the planar medial face when in locking engagement with the receiver.

16. The implantable medical device of claim 15, wherein the deformable head also engages at least one of the planar upper face and the planar lower face when in locking engagement with the receiver.

17. The implantable medical device of claim 1, wherein:
the means for locking the anchor assembly includes a set screw threadingly received in the deformable head;
wherein in a first position of the set screw in the deformable head the set screw engages the base head and tightens the base head on the desired position in the deformable head and further turning of the set screw from the first position in the deformable head outwardly splays the deformable head in locking engagement with the receiver.

18. The implantable medical device of claim 1, wherein the deformable head includes:
The aperture being threaded for receiving the base portion therein; and
a slot extending along the deformable head.

\* \* \* \* \*

UNITED STATES PATENT AND TRADEMARK OFFICE
CERTIFICATE OF CORRECTION

PATENT NO.      : 7,618,418 B2                                   Page 1 of 1
APPLICATION NO. : 11/019918
DATED           : November 17, 2009
INVENTOR(S)     : Hugues F. Malandain It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1366 days.

Signed and Sealed this

Twenty-sixth Day of October, 2010

David J. Kappos
*Director of the United States Patent and Trademark Office*